(12) United States Patent
Lee

(10) Patent No.: US 9,358,100 B2
(45) Date of Patent: Jun. 7, 2016

(54) HAIR TRANSPLANT MATERIAL

(76) Inventor: Hee Young Lee, Gunsan-si (KR)

( * ) Notice: Subject to any disclaimer, the term of this patent is extended or adjusted under 35 U.S.C. 154(b) by 246 days.

(21) Appl. No.: 14/113,623

(22) PCT Filed: Jul. 26, 2011

(86) PCT No.: PCT/KR2011/005490
§ 371 (c)(1),
(2), (4) Date: Dec. 12, 2013

(87) PCT Pub. No.: WO2012/148042
PCT Pub. Date: Nov. 1, 2012

(65) Prior Publication Data
US 2014/0088706 A1 Mar. 27, 2014

(30) Foreign Application Priority Data
Apr. 26, 2011 (KR) .................. 10-2011-0039163

(51) Int. Cl.
*A61F 2/10* (2006.01)
*A61L 27/36* (2006.01)
*A61L 27/38* (2006.01)
*A61L 2/00* (2006.01)
*A61K 35/36* (2015.01)
*A61L 2/07* (2006.01)
*A61L 2/18* (2006.01)
*A61L 2/20* (2006.01)

(52) U.S. Cl.
CPC ............... *A61F 2/10* (2013.01); *A61L 27/3604* (2013.01); *A61L 27/3834* (2013.01); *A61K 35/36* (2013.01); *A61L 2/0064* (2013.01); *A61L 2/0082* (2013.01); *A61L 2/0088* (2013.01); *A61L 2/07* (2013.01); *A61L 2/18* (2013.01); *A61L 2/202* (2013.01); *A61L 2/204* (2013.01); *A61L 2/206* (2013.01); *A61L 2430/18* (2013.01)

(58) Field of Classification Search
None
See application file for complete search history.

(56) References Cited

U.S. PATENT DOCUMENTS

| | | | |
|---|---|---|---|
| 7,597,885 B2 * | 10/2009 | Barrows .............. | A61L 27/3847 424/93.7 |
| 2006/0228339 A1 * | 10/2006 | Wang .................... | A61K 35/36 424/93.7 |
| 2007/0122387 A1 * | 5/2007 | Cochran ................ | A61K 35/36 424/93.7 |

FOREIGN PATENT DOCUMENTS

| | | | | |
|---|---|---|---|---|
| EP | 0971679 | * | 6/2002 | ............... A61K 7/06 |
| JP | 2002-145701 | * | 5/2002 | ................ A61F 2/10 |

OTHER PUBLICATIONS

Baker et al, Skin Pharmacol, 1994, vol. 7, pp. 335-339.*
Gho et al, Dermatol Surg, 2001, vol. 27, pp. 913.*

* cited by examiner

*Primary Examiner* — Allison Fox
(74) *Attorney, Agent, or Firm* — Sughrue Mion, PLLC

(57) ABSTRACT

A hair transplantation material prepared by a process comprising: refrigerating a hair portion comprising a hair shaft, a hair root, and a cell-collagen layer; and sterilizing the refrigerated hair.

16 Claims, 3 Drawing Sheets

HAIR TRANSPLANT MATERIAL

CROSS REFERENCE TO RELATED APPLICATIONS

This application is a National Stage of International Application No. PCT/KR2011/005490 filed Jul. 26, 2011, claiming priority based on Korean Patent Application No. 10-2011-0039163 filed Apr. 26, 2011, the contents of all of which are incorporated herein by reference in their entirety.

BACKGROUND OF THE INVENTION

1. Field of the Invention

The present invention relates to a hair transplantation material. More particularly, the present invention relates to a hair transplantation material applicable to a necessary body site including the scalp.

2. Description of the Related Art

Hair transplantation is a technique by which hairs are artificially transplanted to a bald or balding part of the body, with the aim of preventing persons suffering from hair loss against stress and social anxiety.

Hair transplantation may be performed in two different ways, i.e., with natural hairs or artificial hairs. For natural hair transplantation, autologous hair roots (follicles) are harvested from a donor site and transplanted to a recipient site, that is, a bald or balding part where the hairs are to be grown.

In autologous hair transplantation, hair follicles are individually separated and inserted into recipient sites using a placement tool. Because individual follicles are removed, only small puncture scars remain, with only slight hemorrhaging therefrom. In addition, autologous hair transplantation is advantageous in term of freedom in determining the direction of hair growth and the position at which to place the transplanted hair. However, the removal of individual hair follicles requires a significant period of time as well as a significant level of experience.

Particularly, autologous hair transplantation may have a problem in that the donor site for supplying hairs must be found in the same person. That is, it is somewhat difficult to harvest a significant number of hairs from the patient characterized by a deficiency in hair, so that a broad area of baldness cannot be covered. Frequently, hairs to be planted are insufficient for necessary coverage, which is one of the most significant problems with autologous hair transplantation. In addition, autologous hair transplantation suffers from the disadvantage of temporal limitation since removed hairs are difficult to store, and thus must be transplanted immediately.

There is therefore a need for a hair transplantation material that can harvest hairs, including hair, armpit hair, pubic hair, etc. from patients themselves, as well as from other persons and even from animals.

SUMMARY OF THE INVENTION

Disclosure

Technical Problem

Accordingly, the present invention has been made keeping in mind the above problems occurring in the prior art, and an object of the present invention is to provide a hair transplantation material which allows autologous hair from any donor sites of the body to be transplanted to a recipient site, i.e., bald or balding part of the body.

Another object of the present invention is to provide a hair transplantation material which allows for the use of any homologous or heterologous hair in hair transplantation.

Technical Solution

In order to accomplish the above objects, the present invention provides a hair transplantation material prepared by a process comprising: refrigerating a hair portion comprising a hair shaft, a hair root, and a cell-collagen layer; and sterilizing the refrigerated hair.

In one embodiment, the process further comprises inactivating the sterilized hair.

In another embodiment, the process further comprises culturing stem cells around the hair root after the inactivating step.

In another embodiment, the refrigerating step is conducted by cooling the hair portion in saline or PBS (phosphate buffered saline).

In another embodiment, the refrigerating step is conducted by lyophilization.

In another embodiment, the hair root of the hair portion comprises an internal root sheath.

In another embodiment, the sterilizing step is conducted in a liquid or gas phase, said liquid phase utilizing zephanone or widex, said gas phase utilizing one selected from among ethylene oxide, formalin, ozone and plasma.

In another embodiment, the sterilizing step is conducted with hot water or steam maintained at a temperature of 43° C. or higher.

In another embodiment, the inactivating step is conducted with microwaves or alcohol (ethanol).

In another embodiment, the inactivating step is directed towards nucleic acids (DNA, RNA) using an enzyme or a gamma ray.

In another embodiment, the inactivating step includes decellularization by disrupting cells with sodium chloride or sodium dodecyl sulfate (SDS).

In another embodiment, the process further comprises fixing many strands of the hair in a regular alignment on a film strip by attaching the hair shaft to the film strip.

In another embodiment, the culturing step is conducted by incubating the sterilized hair in a medium containing the stem cells of mononuclear cells at a warm temperature.

In another embodiment, the stem cells are selected from the group consisting of autologous ADSC (adipose tissue derived stromal/stem cells), follicular mononuclear cells, autologous bone marrow/peripheral blood mononuclear cells, umbilical cord/cord blood mononuclear cells, and a combination thereof.

In another embodiment, the medium is supplemented with EGF (epidermal growth factor).

In another embodiment, the culturing step comprises differentiation into epithelial cells.

In another embodiment, the hair is harvested from an animal.

Advantageous Effect

For use as the hair transplantation material, as described above, a hair, if autogenous, can be obtained from any donor site of the body, and can be transplanted into a desired recipient site in accordance with the present invention In addition, hairs, whether heterogenous or xenogenous, such as even from animals, can be used as a hair transplantation material applicable to a recipient site, and thus can compensate for the lack of autologous hair transplantation materials.

DESCRIPTION OF THE PREFERRED EMBODIMENTS

Best Mode

Figure 1:
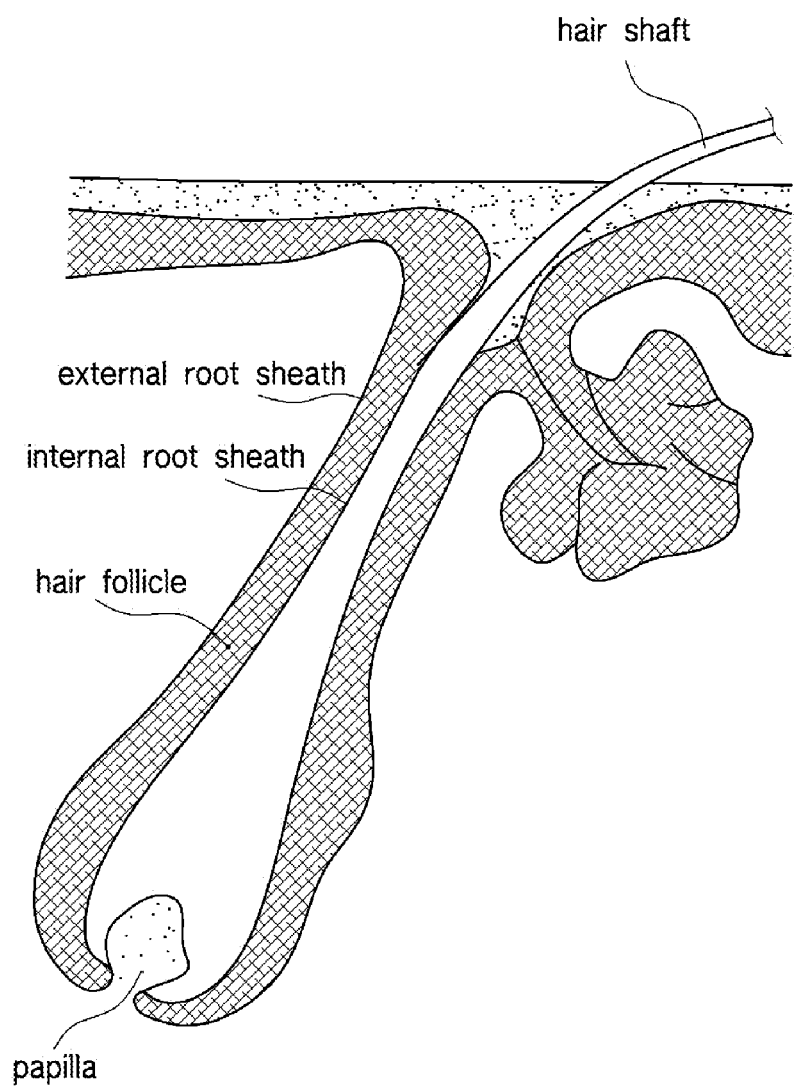
FIG. 1 illustrates the structure of a hair follicle.

Below, a description will be given of preferred embodiments of the present invention in conjunction with the accompanying drawings. Throughout the accompanying drawings, the same reference numerals are used to designate the same or similar components. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, the description thereof will be omitted.

The terms "approximately" and/or "substantially," as used to designate degree, are used as the meanings of the numerals or approximations of the numerals when the manufacturing techniques and allowable errors of materials that are inherent to the corresponding meanings are presented, and are used to prevent an unconscientious infringer from unfairly using disclosed contents in which accurate or absolute numerals are given to assist understanding of the present invention.

As used herein the term "hair" is intended to encompass any hair harvested from head hairs, beards, pubic hair, etc. of humans and animals. The hair follicle refers to an epithelial tissue in a sac form surrounding the hair root. As used herein, the term "hair root" refers to the part of a hair that is embedded in a hair follicle.

For use in transplantation to, for example, the scalp, hairs may be harvested with insufficiency in epithelial cells and hair root cells which play an important role in hair growth. Further, epithelial cells attached to the harvested hairs must be removed before the allotransplantation or xenotransplantation of the hairs. In this context, mononuclear cells from the recipient are cultured in vitro as stem cells and then associated to the hairs to be transplanted, so as to compensate for the deficiency of epithelial cells and hair root cells or to act as a puzzle piece substituting for the removed cells, whereby conditions for growing the hairs can be established.

Based on the observation that paedogamy in lower animals utilizes the remainder as a basal body to generate the most suitable cells for the adjacent organ, this process can be achieved by the activation of human stem cells.

Important to the cells to be differentiated are not the cells remaining in the hair harvested from a source, but the 3D structure of the hair because it acts as a scaffold. The remaining cells, if unmatched in histocompatibility, are advantageously removed due to their antigenicity. Hence, a process is necessary for removing all substances which may be causative of antigenicity and reactivity.

In addition, the hair portions, which may be obtained from other persons or animals, are likely to denature or be contaminated with harmful germs during storage or transportation, and the processes of sterilizing the hair portions and culturing stem cells of the recipient are accordingly necessary.

Figure 2:
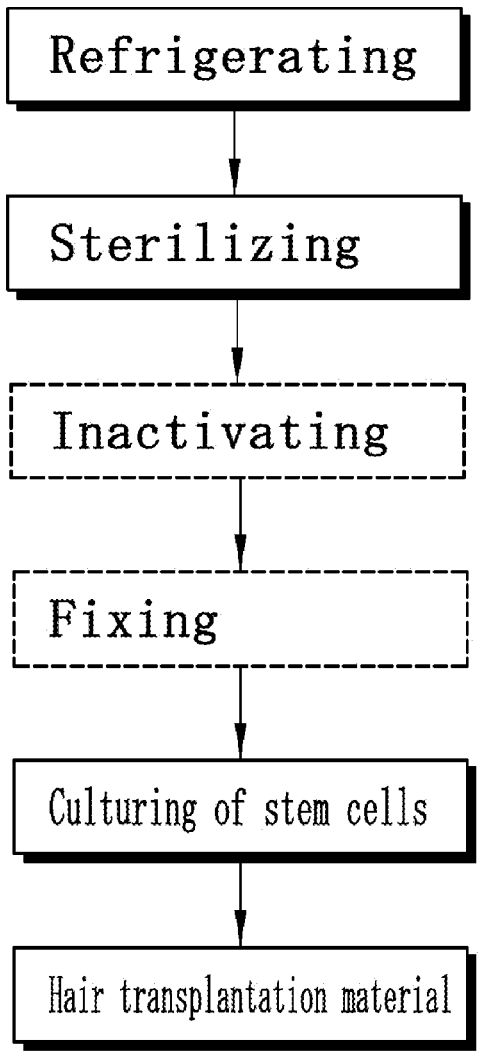
FIG. 2 is a flow chart of the preparation of a hair transplantation material according to one embodiment of the present invention.

FIG. 1 is a schematic view of a hair structure including a hair follicle, and FIG. 2 is a flow chart of the manufacture of a hair transplantation material.

The present invention provides a hair transplantation material prepared by refrigerating a hair portion comprising a hair shaft, a hair root, and a cell-collagen layer attached to the hair root, sterilizing the hair portion, and optionally inactivating the sterilized hair. Further, culturing stem cells around the hair root may be optionally included.

The hair portion comprising a hair shaft, a hair root, and a cell-collagen layer attached to the hair root may be uprooted with, for example, an external mechanical force.

Before being refrigerated, the hair is preferably drawn carefully as to comprise a hair shaft and a hair root, with a cell-collagen layer remaining attached to the hair root. The hair in this 3D structure can be suitable for use in transplantation.

Preferable is a hair in the anagen phase. Hairs in the anagen phase are growing, so that they are likely to grow even after transplantation.

In the present invention, the hair material for use in transplantation preferably comprises an internal root sheath. Preferably, the hair does not comprise an epithelial cell layer, a vessel, and a papilla. If they are present, the epithelial cell layer, the vessel, and the papilla are preferably removed from the hair material.

According to the present invention, the hair material is allowed to undergo a refrigeration process. Refrigeration is an indispensible process because it ensures the sample retains the 3D structure of the scaffold and maintains the hair material for a long period of time.

Refrigeration may be lyophilization or cold storage.

Particularly as for lyophilization, it can keep the hair material intact in a 3D structure, as well as for a long period of time. Lyophilization is a process in which a substance is frozen and subjected to sublimation at a low pressure to extract water therefrom, whereby the substance is easier to store at room temperature while maintaining structural integrity. Once lyophilized, the substance can be stored for a very long period of time in a nitrogen atmosphere.

For cold storage, for example, the hair material is cooled in saline (0.9% NaCl) or an isotonic (e.g., PBS (phosphate buffered saline)). Cold storage may be set at a temperature of 0~4° C., or at less than 0° C. when an antifreeze is used. Optionally, the hair material may be vacuum packaged upon cold storage so as to prevent dryness.

After the refrigeration process, the hair material may be optionally subjected to sterilization. This sterilization to eliminate harmful germs may be performed with liquid or gas, or in other various manner.

The liquid for use in sterilization may be zephanone or widex. Examples of the gas suitable for the sterilization include ethylene oxide, formalin, ozone, and plasma.

Moreover, the hair material may be sterilized with hot water or steam. Sterilization with hot water or steam is preferably finished within a short time less there would occur protein denaturation. In this regard, water or steam maintained at 43° C. or higher may be used in the sterilization process.

Next, the bulb of the hair material may be optionally inactivated. The inactivation aims to prevent the antigenicity and biological reactivity which might be caused by non-autogenous cells upon transplantation.

The inactivation of cells can be accomplished using microwaves, alcohol (i.e., ethanol), or formaldehyde. For formaldehyde, it must be removed after use.

In addition, the inactivation may be directed towards nucleic acids (e.g., DNA, RNA, etc.). The inactivation of nucleic acids may be accomplished with an enzyme or a gamma ray. Non-limiting examples of the enzyme include endonucleases.

Furthermore, the inactivation process may include decellularization using a hypo- or hypertonic solution. Decellularization with a hypotonic solution may be exemplified by cell disruption as a result of immersing the hair bulb in distilled water. Cells may be also lysed in a hypertonic solution such as a concentrated solution of sodium chloride or sodium dodecyl sulfate (SDS).

Following the inactivation, stem cells from the recipient are cultured in the hair root of the hair material so as to act as a hair follicle. Prior to the application of stem cells, the hair material may be optionally fixed. When hair materials are randomly aligned and are adjacent to each other, the collagen may be highly prone to mutual adhesion and deformation, and hinders the penetration of a sterilizing agent. For this reason, the hair materials are preferably fixed.

Figure 3:
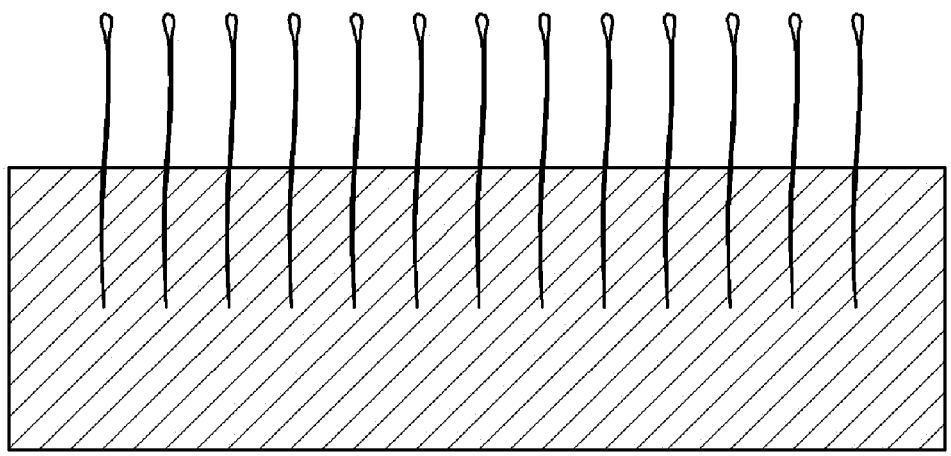
FIGS. 3 and 4 are schematic views of the fixation of hair strands on films.
Figure 4:
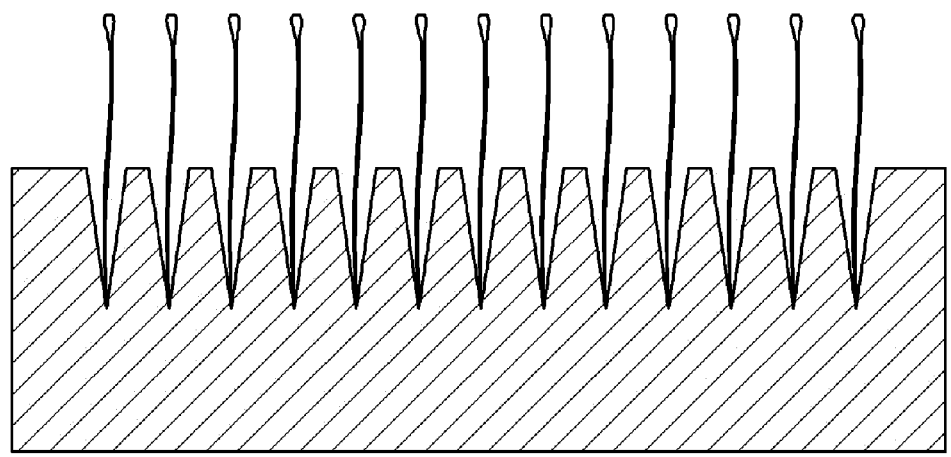

By way of example, the hair materials can be aligned in a regular line by fixing the hair shaft onto a film strip. FIG. 3 is a schematic view of hair materials fixedly aligned in a regular line on a film strip. The film strip may be preferably made of a thermoplastic resin, and hair materials may be fixed by pressing the hair shafts thereof against the film strip. Alternatively, the film strip may be coated with a binder to facilitate the fixation of the hair materials.

In addition, a film strip in which slits are formed at regular intervals may be used as a tool for aligning a bundle of the hair materials in a regular line.

Subsequently, the stem cells are grown around the hair root. In this context, the hair materials may be incubated in a medium containing stem cells at a suitable temperature.

The medium may be a typical one for an animal cell culture, for example, DMEM supplemented with amino acid, vitamins, inorganic ingredients, glucose, lipids, etc.

For use in the present invention, the stem cells are preferably selected from the group consisting of autologous adipose tissue derived stromal/stem cell (ADSC), follicular mononuclear cells, autologous bone marrow/peripheral blood mononuclear cells, umbilical cord/cord blood mononuclear cells, and a combination thereof.

Preferably, the medium may contain an additive such as EGF (epidermal growth factor). During the culturing process of stem cells, they are allowed to differentiate into epithelial cells to form hair follicles.

After completion of the culturing process, hair materials with mature hair follicles are selected for individual transplantation. Hair materials in which viable stem cells are attached to the collagen of the hair root thereof may be selected while monitoring under a microscope. Alternatively, the hair materials may be selected and loaded individually into a transplantation syringe while being monitored for follicle formation with the naked eye.

These serial processes which are focused on the removal of antigenicity and reactivity from hair materials allow for the transplantation of heterologous or xenologous hair materials, in substitution for autologous hair materials when they are deficient in quantity. That is, hair materials from animals such as swine, canines, etc., as well as from other persons can be transplanted into patients.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A hair transplantation material, prepared using a process comprising:
   lyophilizing a hair portion comprising a hair shaft, a hair root, and a cell-collagen layer; and
   sterilizing the lyophilized hair.

2. The hair transplantation material of claim 1, wherein the lyophilizing step is conducted by cooling the hair portion in saline or PBS (phosphate buffered saline).

3. The hair transplantation material of claim 1, wherein the sterilizing step is conducted in a liquid or gas phase, said gas phase utilizing one selected from among ethylene oxide, formalin, ozone and plasma.

4. The hair transplantation material of claim 1, wherein the sterilizing step is conducted with hot water or steam maintained at a temperature of 43° C. or higher.

5. The hair transplantation material of claim 1, wherein the process further comprises inactivating the sterilized hair.

6. The hair transplantation material of claim 5, wherein the inactivating step is conducted with microwaves or alcohol.

7. The hair transplantation material of claim 5, wherein the inactivating step involves using an enzyme or a gamma ray.

8. The hair transplantation material of claim 5, wherein the inactivating step includes decellularization by disrupting cells with sodium chloride or sodium dodecyl sulfate (SDS).

9. The hair transplantation material of claim 5, wherein the process further comprises fixing many strands of the hair in a regular alignment on a film strip by attaching the hair shaft to the film strip.

10. The hair transplantation material of claim 5, wherein the process further comprises culturing stem cells around the hair root after the inactivating step.

11. The hair transplantation material of claim 10, wherein the culturing step is conducted by incubating the sterilized hair in a medium containing the stem cells at a warm temperature.

12. The hair transplantation material of claim 11, wherein the stem cells are selected from the group consisting of autologous ADSC (adipose tissue derived stromal/stem cells), follicular mononuclear cells, autologous bone marrow/peripheral blood mononuclear cells, umbilical cord/cord blood mononuclear cells, and a combination thereof.

13. The hair transplantation material of claim 11, wherein the medium is supplemented with EGF (epidermal growth factor).

14. The hair transplantation material of claim 10, wherein the culturing step comprises differentiation into epithelial cells.

15. The hair transplantation material of claim 1, wherein the hair root of the hair portion comprises an internal root sheath.

16. The hair transplantation material of claim 1, wherein the hair is harvested from an animal.

* * * * *